United States Patent [19]
Vidal et al.

[11] Patent Number: 5,958,382
[45] Date of Patent: Sep. 28, 1999

[54] 4,4-DIHYDROXY-5-PYRAZOLINONES AND COSMETIC/DERMATOLOGICAL COMPOSITIONS COMPRISED THEREOF

[75] Inventors: Laurent Vidal, Paris; Gérard Malle, S/Morin; Jean-Claude Garson, Suresnes, all of France

[73] Assignee: Societe L'Oreal S.A., Paris, France

[21] Appl. No.: 09/157,412

[22] Filed: Sep. 21, 1998

[30] Foreign Application Priority Data

Sep. 19, 1997 [FR] France ................ 97 11702

[51] Int. Cl.$^6$ .............. A61K 7/42; A61K 7/44; C07D 231/28; C07D 231/40
[52] U.S. Cl. .............. 424/59; 424/60; 424/63; 424/69; 424/70.1; 424/70.6; 514/844; 514/847; 546/276.1; 548/365.4; 548/365.7; 548/366.4; 548/367.1
[58] Field of Search ............ 548/365.4, 365.7, 548/366.4, 367.1; 424/59

[56] References Cited

FOREIGN PATENT DOCUMENTS 2018056  5/1970  France .
195 01 304  7/1996  Germany .

OTHER PUBLICATIONS

Pimenova et al, Chemical Abstracts, vol. 119, No. 8728, 1993.

*Primary Examiner*—Robert W. Ramsuer
*Attorney, Agent, or Firm*—Burns, Doane, Swecker & Mathis, L.L.P.

[57] ABSTRACT

Novel 4,4-dihydroxy-5-pyrazolinones having the structural formula (I):

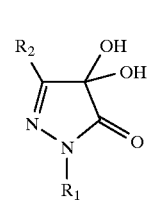

and cosmetic/dermatological formulations comprised thereof are useful for artificially coloring, e.g., tanning/browning, human skin and/or hair, and are well suited for imparting a healthy appearance to facial skin by enhancing the radiance of the complexion, while at the same time retaining transparency.

16 Claims, No Drawings

4,4-DIHYDROXY-5-PYRAZOLINONES AND COSMETIC/DERMATOLOGICAL COMPOSITIONS COMPRISED THEREOF

CROSS-REFERENCE TO PRIORITY APPLICATION

This application claims priority under 35 U.S.C. §119 of FR-97/11702, filed Sep. 19, 1997, assigned to the assignee hereof and hereby expressly incorporated by reference.

BACKGROUND OF THE INVENTION

1. Technical Field of the Invention

The present invention relates to novel 4,4-dihydroxy-5-pyrazolinones, to processes for their preparation and the formulation thereof into cosmetic/dermatological compositions well suited for coloring the skin and/or the hair, and also for coloring certain areas of the skin, in particular the face, in order to impart a healthy appearance thereto by enhancing the radiance of the complexion while at the same time retaining transparency.

This invention also relates to the use of the subject compounds in the cosmetics field for the coloration of the skin and, more particularly, for imparting a tanned appearance to the skin.

2. Description of the Prior Art

It is known to this art that dihydroxyacetone, or DHA, is a particularly advantageous compound commonly used in cosmetics as an agent for artificially tanning or browning the skin; when applied to the skin, in particular to the face, it affords a tanning or browning effect which is very similar in appearance to that which can result from prolonged exposure to the sun (a natural tan) or under a UV lamp. Such use also presents the advantage of entirely avoiding the risks of skin reaction generally associated with the aforementioned prolonged exposures (erythema, burning, loss of elasticity, appearance of wrinkles, premature aging of the skin, and the like).

However, the use of DHA has certain drawbacks.

For example, although the color produced on the skin by applying a composition containing DHA is very close to that obtained in a natural tan, certain users may still consider it to be too yellow.

Other drawbacks also appear during the storage of compositions containing DHA. Thus, DHA has an annoying tendency, which may be more or less pronounced depending on the nature of the medium in which it is formulated, to degrade over time, this degradation generally leading in the long term to an undesirable yellowing of the compositions containing same. Over time, such compositions may also develop a nauseating odor. Lastly, the pH of compositions containing DHA decreases over time, making them in the long run incompatible for topical application. These various phenomena have the effect of greatly reducing the activity of DHA, and in particular its ability to color the skin, when such compositions are topically applied onto the skin.

Moreover, the intensity of the coloration obtained on the skin, and especially the speed with which this coloration develops, are often considered to be insufficient by users of DHA-based self-tanning products, since the time required for the desired intensity to appear on the skin is generally several hours.

In order to increase the speed of appearance of the coloration due to DHA, it has been sought to combine it with other active species. Thus, EP-A-547,864 describes providing DHA in the presence of an amino acid and a silicone, the DHA and the amino acid being stored in separate compartments before they are applied to the skin. Mention may also be made of WO-A-94/04130 which describes a device for supplying DHA at the same time as a primary amine, these two compounds also being stored in separate compartments.

Nonetheless, these devices present the drawback of being complicated and of not providing any real improvement as regards the waiting time required in order to obtain a satisfactory coloration on the skin. Lastly, in addition, they do not totally solve the problems due to the storage of compositions containing DHA.

Thus, it appears that DHA as an agent for artificially coloring the skin is not completely satisfactory and serious need continues to exist for other active agents which, preferably, do not present any of the disadvantages and drawbacks above.

SUMMARY OF THE INVENTION

Unexpectedly, novel artificial tanning 4,4-dihydroxy-5-pyrazolinones have now been developed, which, when formulated into cosmetic/dermatological compositions and topically applied onto the skin markedly reduce the time required for the tanning thereof. These compositions also exhibit excellent stability and impart to the skin a color very close to that of a natural tan. Lastly, the staying power of the coloration on the skin is also noteworthy.

DETAILED DESCRIPTION OF BEST MODE AND SPECIFIC/PREFERRED EMBODIMENTS OF THE INVENTION

More particularly according to the invention, the subject compounds are also useful to specifically color certain areas of the skin, in particular the face, in order to provide a healthy appearance. Traditionally, makeup compositions and in particular foundations based on pigments and fillers have thus been used, which present the drawback of acting as a screen on the skin and, consequently, masking it too much.

The compositions of the invention based on the subject 4,4-dihydroxy-5-pyrazolinones enhance the radiance of the complexion while at the same time retaining its transparency.

Moreover, these compositions are also particularly advantageous for dyeing the hair.

The subject novel 4,4-dihydroxy-5-pyrazolinone compounds have the structural formula (I) below:

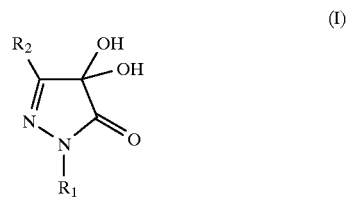

in which $R_1$ is a hydrogen atom; a linear or branched $C_1$–$C_{18}$ alkyl radical optionally substituted with a hydroxyl (OH), sulfonyl ($SO_3H$), carboxyl (COOH), $C_2$–$C_4$ hydroxyalkyl or cyclopentyl radical; a cyclohexyl or cyclopentyl radical; a radical:

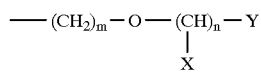

wherein m is equal to 1, 2 or 3, n is equal to 1, 2 or 3, X is a hydrogen atom or a methyl radical, and Y is a methyl, hydroxyl or linear or branched $C_1$–$C_5$ alkoxy radical; a radical —$(CH_2)_p$—OR' wherein R' is a substituted or unsubstituted phenyl or naphthyl radical and p is equal to 1 or 2; a radical —$(CH_2)_q$—R" wherein q is equal to 1, 2 or 3 and R" is a phenyl radical which is unsubstituted or substituted with not more than two radicals selected from among methyl, trifluoromethyl, methoxy and sulfonyl radicals, a naphthyl radical, a thienyl radical, a furyl radical, a pyridyl radical or a piperidyl radical, a radical:

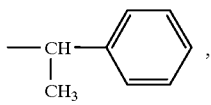

a radical:

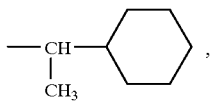

or a radical:

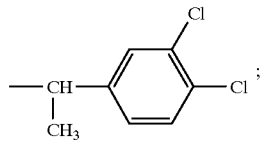

a phenyl radical; a phenyl radical substituted with one or two nitro radicals; a phenyl radical substituted with one to five radicals selected from among —COOH, —CH$_2$COOH, —Cl, —Br, —F, —OH, —SO$_3$H, —CH$_{2\ OH,\ —OCF3}$, —CF$_3$, —SO$_2$CH$_3$, —SO$_2$NH$_2$, —SO$_2$NHC$_2$H$_5$, —SO$_2$NHCH$_2$CH$_2$OH, —CON(CH$_3$)$_2$, —CON(C$_2$H$_5$)$_2$, —CH$_2$N(CH$_3$)$_2$, —CH$_2$N(C2H$_5$)$_2$, —NHCOCH$_3$, —NHCOC$_2$H$_5$, a $C_1$–$C_8$ alkyl radical or a radical —ZR$_3$ wherein Z is an oxygen or sulfur atom and R$_3$ is a hydrogen atom or a linear or branched $C_1$–$C_{18}$ alkyl radical; a naphthyl radical optionally substituted with an —SO$_3$H radical; a benzyl radical; a benzyl radical substituted with a —COOH, —OCH$_3$ or —SO$_3$H radical; a pyridyl radical; a pyrimidinyl radical; a pyrazinyl radical; a triazinyl radical; a benzotriazolyl radical; a benzimidazolyl radical; a thienyl radical; an imidazolyl radical; a thiazolyl radical; a 1,2,4-triazolyl radical; an indazolyl radical; an indolyl radical; a quinolyl radical or an isoquinolyl radical; and R$_2$ is a hydrogen atom; a linear or branched $C_1$–$C_{18}$ alkyl radical optionally substituted with one or more hydroxyl radicals or $C_1$–$C_4$ alkoxy radicals; or a linear or branched $C_3$–$C_{18}$ alkenyl radical optionally substituted with one or more hydroxyl radicals or $C_1$–$C_4$ alkoxy radicals; a phenyl radical; a phenyl radical substituted with a halogen atom, a nitro radical or a trifluoromethyl radical; a phenyl radical substituted with not more than three radicals selected from among $C_1$–$C_4$ alkyl, $C_1$–$C_4$ alkoxy, $C_1$–$C_4$ dialkylamino and $C_1$–$C_2$ alkylthio radicals; a benzyl radical; a benzyl radical substituted with a halogen atom, a $C_1$–$C_4$ alkyl radical, a $C_1$–$C_4$ alkoxy radical, a trifluoromethyl radical or a $C_1$–$C_4$ dialkylamino radical; a radical —$(CH_2)_r$—R$_4$ wherein r is equal to 1, 2 or 3 and R$_4$ is selected from among an —SO$_3$H radical, a $C_1$–$C_2$ alkylthio radical or a benzylthio radical; a methoxycarbonyl or ethoxycarbonyl radical; a phenyl radical; a $C_1$–$C_4$ alkoxy radical or a phenoxy radical optionally substituted with one or more halogen atoms (for example F, Cl or Br); a $C_1$–$C_4$ alkoxy radical; a phenoxy radical optionally substituted with one or more halogen atoms; a trifluoromethyl radical; an acetamido radical; a $C_1$–$C_4$ dialkylamino radical; a carboxyl radical; a methoxycarbonyl radical; an ethoxycarbonyl radical; a radical —NH—CO—R$_5$ wherein R$_5$ is a linear or branched $C_1$–$C_{18}$ alkyl radical or alternatively a $C_3$–$C_{18}$ alkenyl radical; a thienyl radical; a furyl radical; a pyridyl radical or a pyrazolyl radical; or a halogen atom such as fluorine, chlorine or bromine.

It should be appreciated that when R$_2$ denotes a radical attached to the pyrazoline ring via a carbon atom, then R$_2$ can be bonded to said carbon atom via a hetero atom selected from among O, N and S.

Among the 4,4-dihydroxy-5-pyrazolinones defined above, those which are more particularly preferred are those in which R$_1$ is selected from among:

a hydrogen atom; a linear or branched $C_1$–$C_8$ alkyl radical;

a radical —$(CH_2)_2$—OR' wherein R' is a phenyl or naphthyl radical;

a radical —$(CH_2)_q$—R" wherein q is equal to 1 or 2 and R" is a phenyl radical optionally substituted with a trifluoromethyl radical;

a phenyl radical optionally substituted with a nitro radical, a —Cl radical, a $C_1$–$C_4$ alkyl radical or a $C_1$–$C_4$ alkoxy radical; and those in which R$_2$ is selected from among:

a hydrogen atom; a linear or branched $C_1$–$C_4$ alkyl radical; a $C_1$–$C_4$ hydroxyalkyl radical; a methoxymethyl radical;

a phenyl radical optionally substituted with a halogen atom, a nitro radical, a $C_1$–$C_4$ alkyl radical or a $C_1$–$C_4$ alkoxy radical;

a $C_1$–$C_4$ alkoxy radical; a trifluoromethyl radical; an acetamido radical; a $C_1$–$C_4$ dialkylamino radical; a carboxyl radical; a methoxycarbonyl radical; an ethoxycarbonyl radical;

a thienyl radical, a furyl radical, a pyridyl radical or a pyrazolyl radical;

a radical —NHCOR$_5$ in wherein R$_5$ is a linear or branched $C_1$–$C_8$ alkyl radical.

Thus, particularly representative 4,4-dihydroxy-5-pyrazolinones according to the invention include:

1-phenyl-4,4-dihydroxy-5-pyrazolinone; 3-tert-butyl-1-phenyl-4,4-dihydroxy-5-pyrazolinone; 1,3-diphenyl-4,4-dihydroxy-5-pyrazolinone; 1-phenyl 3-(4'-methylphenyl)-4,4-dihydroxy-5-pyrazolinone; 1-phenyl-3-(3'-methoxymethyl)-4,4-dihydroxy-5-pyrazolinone; 1-phenyl-3-(4'-methoxyphenyl)-4,4-dihydroxy-5-pyrazolinone; 1-phenyl-3-(4'-nitrophenyl)-4,4-dihydroxy-5-pyrazolinone; 3-methoxy-1-phenyl-4,4-dihydroxy-5-pyrazolinone; 3-ethoxy-1-phenyl-4,4-dihydroxy-5-pyrazolinone; 3-acetamido-1-phenyl-4,4-dihydroxy-5-pyrazolinone; 3-dimethylamino-1-phenyl-4,4-dihydroxy-5-pyrazolinone; 3-diethylamino-1-phenyl-4,4-dihydroxy-5-pyrazolinone; 3-carboxy-1-phenyl-4,4-dihydroxy-5-pyrazolinone; 3-methoxycarbonyl-1-phenyl-4,4-dihydroxy-5-pyrazolinone; 3-ethoxycarbonyl-1-phenyl-4,4-dihydroxy-5-pyrazolinone; -1-[(3'-trifluoromethyl)benzyl)]-3-methyl-4, 4-dihydroxy-5-pyrazolinone; 1-[(1'-phenyl)ethyl)]-3-methyl-4,4-dihydroxy-5-pyrazolinone; 3-methyl-4,4-dihydroxy-5-pyrazolinone; 1,3-dimethyl-4,4-dihydroxy-5-pyrazolinone; 1-(2'-phenoxy)ethyl-3-methyl-4,4-dihydroxy-5-pyrazolinone; 1-(2'-naphthyloxy)ethyl-3-propyl-4,4-dihydroxy-5-pyrazolinone; 1-(2'-naphthyloxy)-ethyl-3-hydroxymethyl-4,4-dihydroxy-5-pyrazolinone; 3-tert-butyl-1-(2'-phenoxy)ethyl-4,4-dihydroxy-5-pyrazolinone; methoxymethyl-1-(2'-naphthyloxy)-ethyl-4,4-dihydroxy-5-pyrazolinone; 3-methyl-1-(4'-nitrophenyl)-4,4-dihydroxy-5-pyrazolinone; 3-methoxy-4,4-dihydroxy-5-pyrazolinone; 3-ethoxy-4,4-dihydroxy-5-pyrazolinone; 1-methyl-4,4-dihydroxy-5-pyrazolinone; 1-methyl-3-phenyl-4,4-dihydroxy-5-pyrazolinone; 1-methyl-3-(4'-chlorophenyl)-4,4-dihydroxy-5-pyrazolinone; 1-methyl-3-(3'-methoxyphenyl)-4,4-dihydroxy-5-pyrazolinone; 1-methyl-3-(4'-methoxyphenyl)-4,4-dihydroxy-5-pyrazolinone; 1-methyl-3-(3'-nitrophenyl)-4,4-dihydroxy-5-pyrazolinone; 1-methyl-3-(4'-methylphenyl)-4,4-dihydroxy-5-pyrazolinone; 1-methyl-3-(2'-furyl)-4,4-dihydroxy-5-pyrazolinone; 1-methyl-3-(2'-thienyl)-4,4-dihydroxy-5-pyrazolinone; 1-methyl-3-(5'-pyrazolyl)-4,4-dihydroxy-5-pyrazolinone; 1-methyl-3-(4'-pyridyl)-4,4-dihydroxy-5-pyrazolinone; 1-methyl-3-methoxy-4,4-dihydroxy-5-pyrazolinone; 3-ethoxy-1-methyl-4,4-dihydroxy-5-pyrazolinone; 3-dimethylamino-1-methyl-4,4-dihydroxy-5-pyrazolinone; 3-diethylamino-1-methyl-4,4-dihydroxy-5-pyrazolinone; 3-acetamido-1-methyl-4,4-dihydroxy-5-pyrazolinone; 3-carboxy 1-methyl-4,4-dihydroxy-5-pyrazolinone; 3-methoxycarbonyl-1-methyl-4,4-dihydroxy-5-pyrazolinone; 3-ethoxy-carbonyl-1-methyl-4,4-dihydroxy-5-pyrazolinone; 1-ethyl-4,4-dihydroxy-5-pyrazolinone; 1-ethyl-3-methyl-4,4-dihydroxy-5-pyrazolinone; 1-ethyl-3-phenyl-4,4-dihydroxy-5-pyrazolinone; 1-ethyl-3-(4'-chlorophenyl)-4,4-dihydroxy-5-pyrazolinone; 1-ethyl-3-(3'-methoxyphenyl)-4,4-dihydroxy-5-pyrazolinone; 1-ethyl-3-(4'-methoxyphenyl)-4,4-dihydroxy-5-pyrazolinone; 1-ethyl-3-(3'-nitrophenyl)-4,4-dihydroxy-5-pyrazolinone; 1-ethyl-3-(4'-methylphenyl)-4,4-dihydroxy-5-pyrazolinone; 1-ethyl-3-(2'-furyl)-4,4-dihydroxy-5-pyrazolinone; 1-ethyl-3-(2'-thienyl)-4,4-dihydroxy-5-pyrazolinone; 1-ethyl-3-(5'-pyrazolyl)-4,4-dihydroxy-5-pyrazolinone; 1-ethyl-3-methoxy-4,4-dihydroxy-5-pyrazolinone; 1-ethyl-3-ethoxy-4,4-dihydroxy-5-pyrazolinone; 1-ethyl-3-dimethylamino-4,4-dihydroxy-5-pyrazolinone; 1-ethyl-3-diethylamino-4,4-dihydroxy-5-pyrazolinone; 1-ethyl-3-acetamido-4,4-dihydroxy-5-pyrazolinone; 1-ethyl-3-carboxy-4,4-dihydroxy-5-pyrazolinone; 1-ethyl-3-methoxycarbonyl-4,4-dihydroxy-5-pyrazolinone; 1-ethyl-3-ethoxycarbonyl-4,4-dihydroxy-5-pyrazolinone; 1-isopropyl-4,4-dihydroxy-5-pyrazolinone; 1-isopropyl-3-methyl-4,4-dihydroxy-5-pyrazolinone; 1-isopropyl-3-phenyl-4,4-dihydroxy-5-pyrazolinone; 1-isopropyl-3-(4'-chlorophenyl)-4,4-dihydroxy-5-pyrazolinone; 1-isopropyl-3-(3'-methoxyphenyl)-4,4-dihydroxy-5-pyrazolinone; 1-isopropyl-3-(4'-methoxyphenyl)-4,4-dihydroxy-5-pyrazolinone; 1-isopropyl-3-(3'-nitrophenyl)-4,4-dihydroxy-5-pyrazolinone; 1-isopropyl-3-(4'-methylphenyl)-4,4-dihydroxy-5-pyrazolinone; 1-isopropyl-3-(2'-furyl)-4,4-dihydroxy-5-pyrazolinone; 1-isopropyl-3-(2'-thienyl)-4,4-dihydroxy-5-pyrazolinone; 1-isopropyl-3-(5'-pyrazolyl)-4,4-dihydroxy-5-pyrazolinone; 1-isopropyl-3-methoxy-4,4-dihydroxy-5-pyrazolinone; 1-isopropyl-3-ethoxy-4,4-dihydroxy-5-pyrazolinone; 1-isopropyl-3-dimethylamino-4,4-dihydroxy-5-pyrazolinone; 1-isopropyl-3-diethylamino-4,4-dihydroxy-5-pyrazolinone; 1-isopropyl-3-acetamido-4,4-dihydroxy-5-pyrazolinone; 1-isopropyl-3-carboxy-4,4-dihydroxy-5-pyrazolinone; 1-isopropyl-3-methoxycarbonyl-4,4-dihydroxy-5-pyrazolinone; 1-isopropyl-3-ethoxycarbonyl-4,4-dihydroxy-5-pyrazolinone; 1-tert-butyl-4,4-dihydroxy-5-pyrazolinone; 1-tert-butyl-3-methyl-4,4-dihydroxy-5-pyrazolinone; 1-tert-butyl-3-phenyl-4,4-dihydroxy-5-pyrazolinone; 1-tert-butyl-3-(4'-chlorophenyl)-4,4-dihydroxy-5-pyrazolinone; 1-tert-butyl-3-(3'-methoxyphenyl)-4,4-dihydroxy-5-pyrazolinone; 1-tert-butyl-3-(4'-methoxyphenyl)-4,4-dihydroxy-5-pyrazolinone; 1-tert-butyl-3-(3'-nitrophenyl)-4,4-dihydroxy-5-pyrazolinone; 1-tert-butyl-3-(4'-methylphenyl)-4,4-dihydroxy-5-pyrazolinone; 1-tert-butyl-3-(2'-furyl)-4,4-dihydroxy-5-pyrazolinone; 1-tert-butyl-3-(2'-thienyl)-4,4-dihydroxy-5-pyrazolinone; 1-tert-butyl-3-(5'-pyrazolyl)-4,4-dihydroxy-5-pyrazolinone; 1-tert-butyl-3-methoxy-4,4-dihydroxy-5-pyrazolinone; 1-tert-butyl-3-ethoxy-4,4-dihydroxy-5-pyrazolinone; 1-tert-butyl-3-dimethylamino-4,4-dihydroxy-5-pyrazolinone; 1-tert-butyl-3-diethylamino-4,4-dihydroxy-5-pyrazolinone; 1-tert-butyl-3-acetamido-4,4-dihydroxy-5-pyrazolinone; 1-tert-butyl-3-carboxy-4,4-dihydroxy-5-pyrazolinone; 1-tert-butyl-3-methoxycarbonyl-4,4-dihydroxy-5-pyrazolinone; 1-tert-butyl-3-ethoxycarbonyl-4,4-dihydroxy-5-pyrazolinone; 1-octyl-4,4-dihydroxy-5-pyrazolinone; 1-octyl-3-methyl-4,4-dihydroxy-5-pyrazolinone; 1-octyl-3-phenyl-4,4-dihydroxy-5-pyrazolinone; 1-octyl-3-(4'-chlorophenyl)-4,4-dihydroxy-5-pyrazolinone; 1-octyl-3-(3'-methoxyphenyl)-4,4-dihydroxy-5-pyrazolinone; 1-octyl-3-(4'-methoxyphenyl)-4,4-dihydroxy-5-pyrazolinone; 1-octyl-3-(3'-nitrophenyl)-4,4-dihydroxy-5-pyrazolinone; 1-(4'-methylphenyl)-4,4-dihydroxy-5-pyrazolinone; 1-(4'-methylphenyl)-3-methyl-4,4-dihydroxy-5-pyrazolinone; 1-(4'-methylphenyl)-3-phenyl-4,4-dihydroxy-5-pyrazolinone; 1-(4'-methylphenyl)-3-(4'-chlorophenyl)-4,4-dihydroxy-5-pyrazolinone; 1-(4'-methylphenyl)-3-(3'-methoxyphenyl)-4,4-dihydroxy-5-pyrazolinone; 1-(4'-methylphenyl)-3-(4'-methoxyphenyl)-4,4-dihydroxy-5-pyrazolinone; 1-(4'-methylphenyl)-3-(3'-nitrophenyl)-4,4-dihydroxy-5-pyrazolinone; 1-(4'-methylphenyl)-3-(4'-methylphenyl)-4,4-dihydroxy-5-pyrazolinone; 1-(4'-methylphenyl)-3-(2'-furyl)-4,4-dihydroxy-5-pyrazolinone; 1-(4'-methylphenyl)-3-(2'-thienyl)-4,4-dihydroxy-5-pyrazolinone; 1-(4'-methylphenyl)-3-(5'-pyrazolyl)-4,4-dihydroxy-5-pyrazolinone; 1-(4'-methylphenyl)-3-methoxy-4,4-dihydroxy-5-pyrazolinone; 1-(4'-methylphenyl)-3-ethoxy-4,4-dihydroxy-5-pyrazolinone; 1-(4'-methylphenyl)-3-dimethylamino-4,4-dihydroxy-5-pyrazolinone; 1-(4'-methylphenyl)-3-diethylamino-4,4-dihydroxy-5-pyrazolinone; 1-(4'-methylphenyl)-3-acetamido-4,4-dihydroxy-5-pyrazolinone; 1-(4'-methylphenyl)-3-carboxy-4,4-dihydroxy-5-pyrazolinone; 1-(4'-methylphenyl)-3-methoxycarbonyl-4,4-dihydroxy-5-pyrazolinone; 1-(4'-methylphenyl)-3-ethoxycarbonyl-4,4-dihydroxy-5-pyrazolinone; 1-benzyl-4,4-dihydroxy-5-pyrazolinone; 1-benzyl-3-methyl-4,4-dihydroxy-5-pyrazolinone; 1-benzyl-3-phenyl-4,4-dihydroxy-5-pyrazolinone; 1-benzyl-3-(4'-methylphenyl)-4,4-dihydroxy-5-pyrazolinone; 1-benzyl-3-(3'-methoxyphenyl)-4,4-dihydroxy-5-pyrazolinone; 1-benzyl-3-(4'-methoxyphenyl)-4,4-dihydroxy-5-pyrazolinone; 1-benzyl-3-(3'-nitrophenyl)-4,4-dihydroxy-5-pyrazolinone; 1-(4'-methoxyphenyl)-4,4-dihydroxy-5-pyrazolinone; 1-(4'-methoxyphenyl)-3-methyl-4,4-dihydroxy-5-pyrazolinone; 1-(4'-methoxyphenyl)-3-(3'-methoxyphenyl) -4,4-dihydroxy-5-pyrazolinone; 1-(4'-methoxyphenyl) -3-phenyl-4,4-dihydroxy-5-pyrazolinone; 1-(4'-methoxyphenyl)-3-(4'-chlorophenyl)-4,4-dihydroxy- 5-pyrazolinone; 1-(4'-methoxyphenyl)-3-(4'-methoxyphenyl)-4,4-dihydroxy-5-pyrazolinone; 1-(4'-methoxyphenyl)-3-(3'-nitrophenyl)-4,4-dihydroxy-5-pyrazolinone; 1-(4'-methoxyphenyl)-3-methoxy-4,4-dihydroxy-5-pyrazolinone; 1-(4'-methoxyphenyl)-3-ethoxy-4,4-dihydroxy-5-pyrazolinone; 1-(4'-methoxyphenyl)-3-dimethylamino-4,4-dihydroxy-5-pyrazolinone; 1-(4'-methoxyphenyl)-3-diethylamino-4,4-dihydroxy-5-pyrazolinone; 1-(4'-methoxyphenyl)-3-acetamido-4,4-dihydroxy-5-pyrazolinone; 1-(4'-methoxyphenyl)-3-carboxy-4,4-dihydroxy-5-pyrazolinone; -1-(4'-methoxyphenyl)-3-methoxycarbonyl-4,4-dihydroxy-5-pyrazolinone; 1-(4'-methoxyphenyl)-3-ethoxycarbonyl-4,4-dihydroxy-5-pyrazolinone; 1-(4'-chlorophenyl)-4,4-dihydroxy-5-pyrazolinone; 1-(4'-chlorophenyl)-3-methyl-4,4-dihydroxy-5-pyrazolinone; 1-(4'-chlorophenyl)-3-phenyl-4,4-dihydroxy-5-pyrazolinone; 1-(4'-chlorophenyl)-3-(4'-methylphenyl)-4,4-dihydroxy-5-pyrazolinone; 1-(4'-chlorophenyl)-3-(3'-methoxyphenyl)-4,4-dihydroxy-5-pyrazolinone; 1-(4'-chlorophenyl)-3-(4'-methoxyphenyl)-4,4-dihydroxy-5-pyrazolinone; 1-(4'-chlorophenyl)-3-(3'-nitrophenyl)-4,4-dihydroxy-5-pyrazolinone; 1-(4'-chlorophenyl)-3-methoxy-4,4-dihydroxy-5-pyrazolinone; 1-(4'-chlorophenyl)-3-ethoxy-4,4-dihydroxy-5-pyrazolinone; 1-(4'-chlorophenyl)-3-dimethylamino-4,4-dihydroxy-5-pyrazolinone; 1-(4'-chlorophenyl)-3-diethylamino-4,4-dihydroxy-5-pyrazolinone; 1-(4'-chlorophenyl)-3-acetamido-4,4-dihydroxy-5-pyrazolinone; 1-(4'-chlorophenyl)-3-carboxy-4,4-dihydroxy-5-pyrazolinone; 1-(4'-chlorophenyl)-3-methoxycarbonyl-4,4-dihydroxy-5-pyrazolinone; 1-(4'-chlorophenyl)-3-ethoxycarbonyl-4,4-dihydroxy-5-pyrazolinone; 1-(4'-nitrophenyl)-4,4-dihydroxy-5-pyrazolinone; 1-(4'-nitrophenyl)-3-methyl-4,4-dihydroxy-5-pyrazolinone; 1-(4'-nitrophenyl)-3-phenyl-4,4-dihydroxy-5-pyrazolinone; 1-(4'-nitrophenyl)-3-(4'-methylphenyl)-4,4-dihydroxy-5-pyrazolinone; 1-(4'-nitrophenyl)-3-(3'-methoxyphenyl) -4,4-dihydroxy-5-pyrazolinone; 1-(4'-nitrophenyl)-3-(4'-methoxyphenyl)-4,4-dihydroxy-5-pyrazolinone; 1-(4'-nitrophenyl)-3-(3'-nitrophenyl)-4,4-dihydroxy-5-pyrazolinone; 1-phenyl-3-trifluoromethyl-4,4-dihydroxy-5-pyrazolinone; 1-methyl-3-trifluoromethyl-4,4-dihydroxy-5-pyrazolinone; 1-isopropyl-3-trifluoromethyl-4,4-dihydroxy-5-pyrazolinone; 1-ethyl-3-trifluoromethyl-4,4-dihydroxy-5-pyrazolinone; and 3-trifluoromethyl-4,4-dihydroxy-5-pyrazolinone.

Among the 4,4-dihydroxy-5-pyrazolinones according to the present invention, most particularly preferred are those in which $R_1$ is selected from among:

hydrogen and methyl, ethyl, isopropyl, tert-butyl and substituted or unsubstituted phenyl radicals; and $R_2$ is selected from among:

hydrogen and methyl, phenyl, methoxyphenyl, methoxy, ethoxy, carboxyl, methoxycarbonyl, ethoxycarbonyl, acetamido, dimethylamino, diethylamino, trifluoromethyl, furyl and pyridyl radicals.

Even more particularly preferred are 3-methyl-4,4-dihydroxy-5-pyrazolinone; 1,3-dimethyl-4,4-dihydroxy-5-pyrazolinone; 1-ethyl-3-methyl-4,4-dihydroxy-5-pyrazolinone; 1-isopropyl-3-methyl-4,4-dihydroxy-5-pyrazolinone; 1-tert-butyl-3-methyl-4,4-dihydroxy-5-pyrazolinone; 1-methyl-3-phenyl-4,4-dihydroxy-5-pyrazolinone; 1-methyl-3-(3'-methoxyphenyl)-4,4-dihydroxy-5-pyrazolinone; 3-(2'-furyl)-1-methyl-4,4-dihydroxy-5-pyrazolinone; 1-methyl-3-(4'-pyridyl)-4,4-dihydroxy-5-pyrazolinone; 1-methyl-3-methoxy-4,4-dihydroxy-5-pyrazolinone; 3-ethoxy-1-methyl-4,4-dihydroxy-5-pyrazolinone; 3-dimethylamino-1-methyl-4,4-dihydroxy-5-pyrazolinone; 3-diethylamino-l-methyl-4,4-dihydroxy-5-pyrazolinone; 3-acetamido-l-methyl-4,4-dihydroxy-5-pyrazolinone; 1-phenyl-4,4-dihydroxy-5-pyrazolinone; 1-methyl-4,4-dihydroxy-5-pyrazolinone; 1-ethyl-4,4-dihydroxy-5-pyrazolinone;1-isopropyl-4,4-dihydroxy-5-pyrazolinone; 1-tert-butyl-4,4-dihydroxy-5-pyrazolinone; 3-methoxy-1-phenyl-4,4-dihydroxy-5-pyrazolinone; 3-ethoxy-1-phenyl-4,4-dihydroxy-5-pyrazolinone; 3-acetamido-1-phenyl-4,4-dihydroxy-5-pyrazolinone; 3-dimethylamino-1-phenyl-4,4-dihydroxy-5-pyrazolinone; 3-diethylamino-1-phenyl-4,4-dihydroxy-5-pyrazolinone; 1-phenyl-3-trifluoromethyl-4,4-dihydroxy-5-pyrazolinone; 1-methyl-3-trifluoromethyl -4,4-dihydroxy-5-pyrazolinone; 1-isopropyl-3-trifluoromethyl-4,4-dihydroxy-5-pyrazolinone; 1-ethyl-3-trifluoromethyl-4,4-dihydroxy-5-pyrazolinone; 3-trifluoromethyl-4,4-dihydroxy-5-pyrazolinone; 3-carboxy-1-phenyl-4,4-dihydroxy-5-pyrazolinone; 3-methoxycarbonyl-1-phenyl-4,4- dihydroxy-5-pyrazolinone; 3-ethoxycarbonyl-1-phenyl -4,4-dihydroxy-5-pyrazolinone; 3-methoxy-4,4-dihydroxy-5-pyrazolinone; 3-ethoxy-4,4-dihydroxy-5-pyrazolinone; 3-carboxy-1-methyl-4,4-dihydroxy-5-pyrazolinone; 3-methoxycarbonyl-1-methyl-4,4-dihydroxy-5-pyrazolinone; 3-ethoxycarbonyl-1-methyl-4,4-dihydroxy-5-pyrazolinone;

The present invention also features cosmetic or dermatological compositions comprising, formulated into a cosmetically acceptable support therefor (vehicle, diluent or carrier), at least one 4,4-dihydroxy-5-pyrazolinone having the to formula (I) above.

In a preferred embodiment of the invention, these compositions are used for artificially tanning the skin.

These novel compositions present the advantage of imparting to the skin a tan which is very close to a natural tan, and in an extremely short period of time. Indeed, a few minutes are sufficient to obtain a tanned complexion.

Thus, the present invention also features a cosmetic treatment regime or regimen for the skin which artificially tans and/or browns same, comprising topically applying an effective amount of a cosmetic composition as described above or a 4,4-dihydroxy-5-pyrazolinone of formula (I) to the skin.

In another embodiment of the invention, the subject cosmetic compositions are used to make up and, more particularly, to color the skin, in particular the face, in order to give it a healthy appearance by enhancing the radiance of the complexion.

This invention also features the making up of the skin, in particular the face, to give it a healthy appearance by enhancing the radiance of the complexion, comprising topically applying an effective amount of a cosmetic composition as described above or a 4,4-dihydroxy-5-pyrazolinone of formula (I) to the skin.

The use of a 4,4-dihydroxy-5-pyrazolinone as indicated above in, or for the formulation of, compositions for making up the skin, in particular the face, imparts a healthy appearance thereto by enhancing the radiance of the complexion.

In another embodiment of the invention, the subject cosmetic compositions are used to dye the hair.

The present invention thus also features a cosmetic treatment of the hair to dye it, comprising applying an effective amount of a composition as described above or a 4,4-dihydroxy-5-pyrazolinone of formula (I) to the hair.

The 4,4-dihydroxy-5-pyrazolinone(s) is(are) used in an effective amount to impart a coloration either to the skin or to the hair, depending on the particular instance. Thus, they are generally present in the compositions according to the invention at a concentration ranging from 0.05% to 10% by weight, preferably from 0.05% to 5% by weight, relative to the total weight of the composition.

When the compositions according to the invention are topically applied onto the skin, their pH ranges from 3 to 10. It preferably ranges from 3 to 7.

When the compositions according to the invention are used to dye the hair, the pH advantageously ranges from 2 to 8. It preferably ranges from 2 to 6.

The vehicle, diluent or carrier (or the cosmetically acceptable support) for the compositions according to the invention is preferably water, either alone or with one or more organic solvents or fatty substances.

The solvents which can be used are preferably selected from among alcohols such as ethyl alcohol and cetyl alcohol, or from propylene glycol, ethylene glycol monoethyl ether and ethylene glycol monobutyl ether.

Exemplary fatty substances include oils and waxes of mineral, animal or plant origin.

By the term "oil" is intended a compound which is liquid at room temperature. By the term "wax" is intended a compound which is solid or substantially solid at room temperature, and whose melting point is generally greater than 35° C.

Exemplary oils include mineral oils (petroleum jelly); plant oils (sweet almond oil, macadamia oil, grapeseed oil); synthetic oils such as perhydrosqualene, fatty alcohols, acids or esters (octyl palmitate, isopropyl lanolate, triglycerides, including those of capric/caprylic acids), oxyethylenated or oxypropylenated fatty esters and ethers; silicone oils (cyclomethicone, polydimethylsiloxanes or PDMSS) or fluoro oils, and polyalkylenes.

Exemplary waxy compounds include jojoba oil, paraffin, carnauba wax, beeswax and hydrogenated castor oil.

The other constituents which can be formulated into the compositions of the invention include, in particular, thickeners, emulsifiers and gelling agents, which are used conventionally in the cosmetics and/or dermatological fields.

Exemplary emulsifiers include fatty acid esters of polyethylene glycol (PEG), fatty acid esters of glycerol (glyceryl stearate) or fatty acid esters of a sugar (sorbitan stearate), as well as the polyoxyethylenated or polyoxypropylenated derivatives thereof, cyclomethicones and dimethicone copolyols, anionic surfactants (potassium or sodium alkyl phosphate), polyalkoxylated fatty alcohols.

Polyalkoxylated fatty alcohols such as oxypropylenated butyl alcohols, oxyethylenated caprylic alcohols and oxyethylenated cetyl alcohols are the preferred.

Exemplary thickeners include crosslinked polyacrylic acids, modified or unmodified guar gums and cellulose gums such as hydroxypropyl guar gum, methylhydroxyethylcellulose, hydroxypropylmethylcellulose or hydroxyethylcellulose.

And exemplary gelling agents include modified clays (bentones), metal salts of fatty acids (aluminum stearate), ethylene/acrylate copolymers, silicas, polyethylenes, calcium silicates or ethylcellulose.

The compositions according to the invention can also contain any other cosmetically or dermatologically acceptable constituent usually included in compositions of this type, such as softeners, antioxidants, opacifiers, stabilizers, emollients, insect repellents, organic sunscreens which are active in the UV-A and/or UV-B range, photoprotective inorganic pigments and nanopigments, moisturizers, vitamins, fragrances, preservatives, fillers, sequestering agents, dyes, colorants, and in particular compounds known for their self-tanning activity such as, for example, dihydroxyacetone, methylglyoxal, glyceraldehyde, erythrulose, alloxan, 2,3-dihydroxysuccinic dialdehyde, 2-amino-3-hydroxysuccinic dialdehyde and 2-benzylamino-3-hydroxysuccinic dialdehyde.

Of course, one a person skilled in this art will take care to select this or these optional complementary compounds and/or the amounts thereof such that the advantageous properties intrinsically associated with the compositions of the invention are not, or are not substantially, adversely affected by the additions envisaged.

The subject compositions are advantageously formulated in the form of a simple or complex emulsion (O/W, W/O, O/W/) or W/O/W emulsion) such as a cream, a lotion, a milk, a gel or a cream-gel, a powder or a solid tube and can optionally be packaged as an aerosol and can be in the form of a mousse or a spray.

Preferably, the subject compositions are formulated as oil-in-water emulsions.

The compositions of the invention can be formulated according to techniques which are well known to this art, in particular those techniques intended for the preparation of emulsions of oil-in-water or water-in-oil type.

The present invention also features a process for the preparation of the compounds of formula (I), comprising the following steps (with $R_1$ and $R_2$ being as defined above):

(i) reacting a monosubstituted hydrazine $R_1NH-NH_2$ with a β-keto ester of the structure:

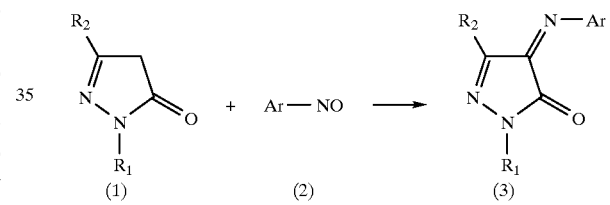

in which $R_6$ is a linear or branched $C_1-C_4$ alkyl radical, preferably in alcoholic medium such as in methanol, ethanol or isopropanol, at a temperature ranging from 65° to 85° C., preferably at the reflux point of the solvent used, to obtain a 5-pyrazolinone (1), which is then reacted with an aromatic nitroso compound (2) to obtain the corresponding 4-arylimino-5-pyrazolinone (3):

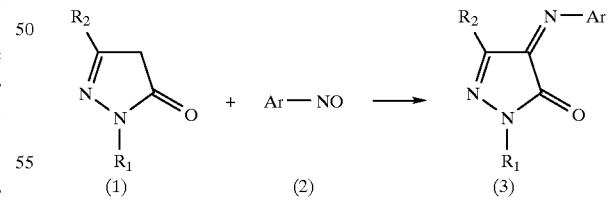

this reaction preferably being carried out in a lower alcohol such as methanol, ethanol or isopropanol, at a temperature ranging from 65° C. to 85° C., at the reflux point of the solvent used, and preferably in the presence of a catalytic amount of a weak base of carbonate or bicarbonate type, (ii) then hydrolyzing the 4-arylimino-5-pyrazolinone (3), preferably in dilute strong acid medium, to obtain the corresponding 4,4-dihydroxy-5-pyrazolinone derivative of formula (I):

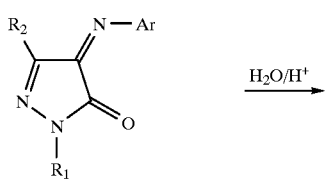

(I)

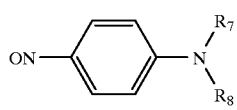

In the above process, the aromatic nitroso derivative from the first step is preferably a p-nitrosodialkylaniline of formula (2):

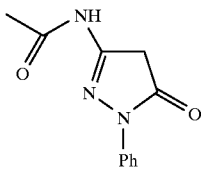

in which $R_7$ and $R_8$ are each a linear or branched $C_1$–$C_4$ alkyl radical.

The acid hydrolysis in the second step of the process according to the invention is preferably carried out using dilute sulfuric acid or aqueous hydrochloric acid at room temperature in the presence of a co-solvent for the 4,4-dihydroxy-5-pyrazolinone, which is immiscible with water, thereby making it possible to advantageously extract the compound as it forms, making it easier to isolate in very high purity. The water-immiscible co-solvent can be a halogenated solvent such as, for example, dichloromethane or 1,2-dichloroethane. In a preferred embodiment of the invention, the water-immiscible cosolvent is an ether such as diethyl ether or diisopropyl ether.

In order to further illustrate the present invention and the advantages thereof, the following specific examples are given, it being understood that same are intended only as illustrative and in nowise limitative.

Example 1

Synthesis of 3-acetamido-4.4-dihydroxy-1-phenyl-5-pyrazolinone

Step 1: Preparation of 3-acetamido-5-hydroxy-1-phenylpyrazole 55 cm³ of acetic anhydride were added dropwise to a solution of 100 g (0.571 mol) of 3-amino-1-phenyl-5-pyrazolinone in 2 liters of acetic acid. The solution was refluxed for 4 hours, 30 minutes and then cooled to about 17° C. The precipitate was filtered off through a No. 4 sinter funnel and washed with diisopropyl ether. The filtrate was concentrated and then chilled. A second crystalline crop formed and was filtered off, washed with diisopropyl ether and dried under vacuum at 40° C. with the first crop. After recrystallization from ethanol, 76.24 g of beige powder were isolated. The ¹H NMR and ¹³C NMR spectra of the compound obtained were in accordance with the expected structure.

Step 2: Preparation of 3-acetamido-4-(N-(4'-dimethylaminophenyl)imino-1-phenyl-5-pyrazolinone

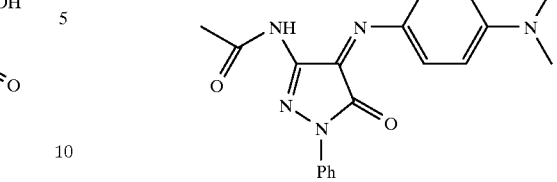

A solution of 52.43 g (0.349 mol) of N,N-dimethyl-4-nitrosoaniline in 1 liter of 1-propanol was added to a solution of 75.84 g (0.349 mol) of 3-acetamido-5-hydroxy-1-phenylpyrazole in 5 liters of 1-propanol warmed to 45° C., followed by 5 g of potassium carbonate (0.035 mol). The reaction mixture was refluxed for 4 hours. The 1-propanol was then distilled off to ¾ and the solution was then chilled. The product was crystallized and was filtered off and washed with cyclohexane on a No. 4 sinter funnel. After drying under vacuum at 40° C., 80.48 g of a black powder were obtained. The ¹H NMR and ¹³C NMR spectra of the compound obtained were in accordance with the expected structure.

Step 3: Preparation of 3-acetamido-1-phenyl-4.4-dihydroxy-5-pyrazolinone of formula (I)

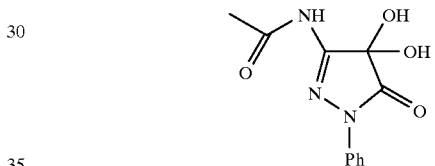

600 ml of 2N sulfuric acid were added dropwise to a solution of 65 g (0.186 mol) of 3-acetamido-4-(N-(4'-dimethylaminophenyl)imino-1-phenyl-5-pyrazolinone in 3.4 liters of THF. The reaction mixture was stirred at room temperature for 3 hours, 30 minutes. The precipitate corresponding to N,N-dimethyl-p-phenylenediamine sulfate was filtered off. After adding diethyl ether and saturated aqueous sodium chloride to the filtrate, the aqueous phase was extracted with diethyl ether. The organic phases were combined, washed to neutrality with saturated aqueous sodium chloride, dried over $Na_2SO_4$ and concentrated to dryness. After recrystallization from a mixture of ethyl acetate and heptane and then drying in air, 15.25 g of a khaki-colored powder corresponding to the expected structure were obtained. The ¹H NMR and ¹³C NMR spectra of the compound obtained were in accordance with the expected structure.

Example 2

One specific example of a self-tanning oil-in-water emulsion in accordance with the invention is as follows:

Phase A

| | |
|---|---|
| (i) 80/20 mixture of cetylstearyl alcohol and of oxyethylenated (33 EO) cetylstearyl alcohol, marketed under the trademark "Dehsconet 390" by Tensia | 7% |
| (ii) mixture of glyceryl mono- and distearate marketed under the trademark | 2% |

-continued

| "Cerasynth SD" by ISP | |
|---|---|
| (iii) cetyl alcohol | 1.5% |
| (iv) polydimethylsiloxane marketed under the trademark "DC2000 Fluid" by Dow Corning | 1.5% |
| (v) $C_{12}/C_{15}$ alkyl benzoate marketed under the trademark "Finsolv TN" by the Finetex | 15% |
| (vi) 3-acetamido-1-phenyl-4,4-dihydroxy-5-pyrazolinone | 1% |

Phase B

| (i) glycerol | | 20% |
|---|---|---|
| (ii) preservatives | | qs |
| (iii) demineralized water | qs | 100% |

This emulsion was prepared according to the following procedure: Phases A and B were heated to 80° C. separately. Phase A was then poured into Phase B while stirring with a Moritz stirrer. The mixture was then homogenized, after which it was permitted to cool to room temperature.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A 4,4-dihydroxy-5-pyrazolinone compound having the structural formula (I):

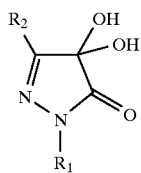

(I)

in which $R_1$ is a hydrogen atom; a linear or branched $C_1$–$C_{18}$ alkyl radical optionally substituted with a hydroxyl (OH), sulfonyl ($SO_3H$), carboxyl (COOH), $C_2$–$C_4$ hydroxyalkyl or cyclopentyl radical; a cyclohexyl or cyclopentyl radical; a radical:

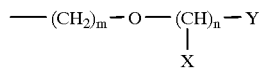

wherein m is equal to 1, 2 or 3, n is equal to 1, 2 or 3, X is a hydrogen atom or a methyl radical, and Y is a methyl, hydroxyl or linear or branched $C_1$–$C_5$ alkoxy radical; a radical —$(CH_2)_p$—OR' wherein R' is a substituted or unsubstituted phenyl or naphthyl radical and p is equal to 1 or 2; a radical —$(CH_2)_q$—R" wherein q is equal to 1, 2 or 3 and R" is a phenyl radical which is unsubstituted or substituted with not more than two radicals selected from among methyl, trifluoromethyl, methoxy and sulfonyl radicals, a naphthyl radical, a thienyl radical, a furyl radical, a pyridyl radical or a piperidyl radical, a radical:

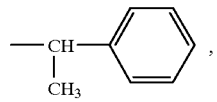

a radical:

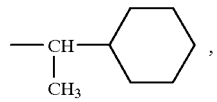

or a radical:

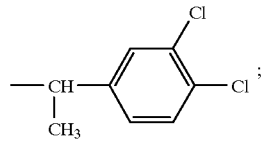

a phenyl radical; a phenyl radical substituted with one or two nitro radicals; a phenyl radical substituted with a phenyl radical substituted with one or two nitro radicals; a phenyl radical substituted with one to five radicals selected from among —COOH, —$CH_2COOH$, —Cl, —Br, —F, —OH, —$SO_3H$, —$CH_2OH$, —$OCF_3$, —$CF_3$, —$SO_2CH_3$, —$SO_2NH_2$, —$SO_2NHC_2H_5$, —$SO_2NHCH_2CH_2OH$, —$CON(CH_3)_2$, —$CON(C_2H_5)_2$, —$CH_2N(CH_3)_2$, —$CH_2N(C2H_5)_2$, —$NHCOCH_3$, —$NHCOC_2H_5$, a $C_1$–$C_8$ alkyl radical or a radical —$ZR_3$ wherein Z is an oxygen or sulfur atom and $R_3$ is a hydrogen atom or a linear or branched $C_1$–$C_{18}$ alkyl radical; a naphthyl radical optionally substituted with an —$SO_3H$ radical; a benzyl radical; a benzyl radical substituted with a —COOH, —$OCH_3$ or —$SO_3H$ radical; a pyridyl radical; a pyrimidinyl radical; a pyrazinyl radical; a triazinyl radical; a benzotriazolyl radical; a benzimidazolyl radical; a thienyl radical; an imidazolyl radical; a thiazolyl radical; a 1,2,4-triazolyl radical; an indazolyl radical; an indolyl radical, a quinolyl radical or an isoquinolyl radical; and $R_2$ is a hydrogen atom; a linear or branched $C_1$–$C_{18}$ alkyl radical optionally substituted with one or more hydroxyl radicals or $C_1$–$C_4$ alkoxy radical; or a linear or branched $C_3$–$C_{18}$ alkenyl radical optionally substituted with one or more hydroxyl radicals or $C_1$–$C_4$ alkoxy radicals; a phenyl radical; a phenyl radical substituted with a halogen atom, a nitro radical or a trifluoromethyl radical; a phenyl radical substituted with not more than three radicals selected from among $C_1$–$C_4$ alkyl, $C_1$–$C_4$ alkoxy, $C_1$–$C_4$ dialkylamino and $C_1$–$C_2$ alkylthio radicals; a benzyl radical; a benzyl radical substituted with a halogen atom, a $C_1$–$C_4$ alkyl radical, a $C_1$–$C_4$ alkoxy radical, a trifluoromethyl radical or a $C_1$–$C_4$ dialkylamino radical; a radical —$(CH_2)_r$—$R_4$ wherein r is equal to 1, 2 or 3 and $R_4$ is selected from among an —$SO_3H$ radical, a $C_1$–$C_2$ alkylthio radical or a benzylthio radical; a methoxycarbonyl or ethoxycarbonyl radical; a phenyl radical; a $C_1$–$C_4$ alkoxy radical or a phenoxy radical optionally substituted with one or more halogen atoms; a $C_1$–$C_4$ alkoxy radical; a phenoxy radical optionally substituted with one or more halogen atoms; a trifluoromethyl radical; an acetamido radical; a $C_1$–$C_4$ dialkylamino radical; a carboxyl radical; a methoxycarbonyl radical; an ethoxycarbonyl radical; a radical —NH—CO—$R_5$ wherein $R_5$ is a linear or branched $C_1$–$C_{18}$ alkyl radical or a $C_3$–$C_{18}$ alkenyl radical; a thienyl radical; a furyl radical; a pyridyl radical or a pyrazolyl radical; or a halogen atom.

2. The 4,4-dihydroxy-5-pyrazolinone compound as defined by claim 1, wherein formula (I), $R_1$ is a hydrogen atom; a linear or branched $C_1$–$C_8$ alkyl radical; a radical —$(CH_2)_2$—OR' wherein R' is a phenyl or naphthyl radical; a radical —$(CH_2)_q$—R" wherein q is equal to 1 or 2 and R" is a phenyl radical optionally substituted with a trifluoromethyl radical; a phenyl radical optionally substituted with a nitro radical, a —Cl radical, a $C_1$–$C_4$ alkyl radical or a $C_1$–$C_4$ alkoxy radical; and $R_2$ is a hydrogen atom; a linear or branched $C_1$–$C_4$ alkyl radical; a $C_1$–$C_4$ hydroxyalkyl radical; a methoxymethyl radical; a phenyl radical optionally substituted with a halogen atom, a nitro radical, a $C_1$–$C_4$ alkyl radical or a $C_1$–$C_4$ alkoxy radical; a $C_1$–$C_4$ alkoxy radical; a trifluoromethyl radical; an acetamido radical; a $C_1$–$C_4$ dialkylamino radical; a carboxyl radical; a methoxycarbonyl radical; an ethoxycarbonyl radical; a thienyl radical; a furyl radical; a pyridyl radical or a pyrazolyl radical; or a radical —$NHCOR_5$ wherein $R_5$ is a linear or branched $C_1$–$C_8$ alkyl radical.

3. The 4,4-dihydroxy-5-pyrazolinone compound as defined by claim 1, selected from among 1-phenyl-4,4-dihydroxy-5-pyrazolinone; 3-tert-butyl-1-phenyl-4,4-dihydroxy-5-pyrazolinone; 1,3-diphenyl-4,4-dihydroxy-5-pyrazolinone; 1-phenyl 3-(4'-methylphenyl)-4,4-dihydroxy-5-pyrazolinone; 1-phenyl-3-(3'-methoxymethyl)-4,4-dihydroxy-5-pyrazolinone; 1-phenyl-3-(4'-methoxyphenyl)-4,4-dihydroxy-5-pyrazolinone; 1-phenyl-3-(4'-nitrophenyl)-4,4-dihydroxy-5-pyrazolinone; 3-methoxy-1-phenyl-4,4-dihydroxy-5-pyrazolinone; 3-ethoxy-1-phenyl-4,4-dihydroxy-5-pyrazolinone; 3-acetamido-1-phenyl-4,4-dihydroxy-5-pyrazolinone; 3-dimethylamino-1-phenyl-4,4-dihydroxy-5-pyrazolinone; 3-diethylamino-1-phenyl-4,4-dihydroxy-5-pyrazolinone; 3-carboxy-1-phenyl-4,4-dihydroxy-5-pyrazolinone; 3-methoxycarbonyl-1-phenyl-4,4-dihydroxy-5-pyrazolinone; 3-ethoxycarbonyl-1-phenyl-4,4-dihydroxy-5-pyrazolinone; -1-[(3'-trifluoromethyl)benzyl)]-3-methyl-4,4-dihydroxy-5-pyrazolinone; 1-[(1'-phenyl)ethyl)]-3-methyl-4,4-dihydroxy-5-pyrazolinone; 3-methyl-4,4-dihydroxy-5-pyrazolinone; 1,3-dimethyl-4,4-dihydroxy-5-pyrazolinone; 1-(2'-phenoxy)ethyl-3-methyl-4,4-dihydroxy-5-pyrazolinone; 1-(2'-naphthyloxy) ethyl-3-propyl-4,4-dihydroxy-5-pyrazolinone; 1-(2'-naphthyloxy)-ethyl-3-hydroxymethyl-4,4-dihydroxy-5-pyrazolinone; 3-tert-butyl-1-(2'-phenoxy)ethyl-4,4-dihydroxy-5-pyrazolinone; methoxymethyl-1-(2'-naphthyloxy)-ethyl-4,4-dihydroxy-5-pyrazolinone; 3-methyl-1-(4'-nitrophenyl)-4,4-dihydroxy-5-pyrazolinone; 3-methoxy-4,4-dihydroxy-5-pyrazolinone; 3-ethoxy-4,4-dihydroxy-5-pyrazolinone; 1-methyl-4,4-dihydroxy-5-pyrazolinone; 1-methyl-3-phenyl-4,4-dihydroxy-5-pyrazolinone; 1-methyl-3-(4'-chlorophenyl)-4,4-dihydroxy-5-pyrazolinone; 1-methyl-3-(3'-methoxyphenyl)-4,4-dihydroxy-5-pyrazolinone; 1-methyl-3-(4'-methoxyphenyl)-4,4- dihydroxy-5-pyrazolinone; 1-methyl-3-(3'-nitrophenyl)-4,4-dihydroxy-5-pyrazolinone; 1-methyl-3-(4'-methylphenyl)-4,4-dihydroxy-5-pyrazolinone; 1-methyl-3-(2'-furyl)-4,4-dihydroxy-5-pyrazolinone; 1-methyl-3-(2'-thienyl)-4,4-dihydroxy-5-pyrazolinone; 1-methyl-3-(5'-pyrazolyl)-4,4-dihydroxy-5-pyrazolinone; 1-methyl-3-(4'-pyridyl)-4,4-dihydroxy-5-pyrazolinone; 1-methyl-3-methoxy-4,4-dihydroxy-5-pyrazolinone; 3-ethoxy-1-methyl-4,4-dihydroxy-5-pyrazolinone; 3-dimethylamino-1-methyl-4,4-dihydroxy-5-pyrazolinone; 3-diethylamino-1-methyl-4,4-dihydroxy-5-pyrazolinone; 3-acetamido-1-methyl-4,4-dihydroxy-5-pyrazolinone; 3-carboxy 1-methyl-4,4-dihydroxy-5-pyrazolinone; 3-methoxycarbonyl-1-methyl-4,4-dihydroxy-5-pyrazolinone; 3-ethoxy-carbonyl-1-methyl-4,4-dihydroxy-5-pyrazolinone; 1-ethyl-4,4-dihydroxy-5-pyrazolinone; 1-ethyl-3-methyl-4,4-dihydroxy-5-pyrazolinone; 1-ethyl-3-phenyl-4,4-dihydroxy-5-pyrazolinone; 1-ethyl-3-(4'-chlorophenyl)-4,4-dihydroxy-5-pyrazolinone; 1-ethyl-3-(3'-methoxyphenyl)-4,4-dihydroxy-5-pyrazolinone; 1-ethyl-3-(4'-methoxyphenyl)-4,4-dihydroxy-5-pyrazolinone; 1-ethyl-3-(3'-nitrophenyl)-4,4-dihydroxy-5-pyrazolinone; 1-ethyl-3-(4'-methylphenyl)-4,4-dihydroxy-5-pyrazolinone; 1-ethyl-3-(2'-furyl)-4,4-dihydroxy-5-pyrazolinone; 1-ethyl-3-(2'-thienyl)-4,4-dihydroxy-5-pyrazolinone; 1-ethyl-3-(5'-pyrazolyl)-4,4-dihydroxy-5-pyrazolinone; 1-ethyl-3-methoxy-4,4-dihydroxy-5-pyrazolinone; 1-ethyl-3-ethoxy-4,4-dihydroxy-5-pyrazolinone; 1-ethyl-3-dimethylamino-4,4-dihydroxy-5-pyrazolinone; 1-ethyl-3-diethylamino-4,4-dihydroxy-5-pyrazolinone; 1-ethyl-3-acetamido-4,4-dihydroxy-5-pyrazolinone; 1-ethyl-3-carboxy-4,4-dihydroxy-5-pyrazolinone; 1-ethyl-3-methoxycarbonyl-4,4-dihydroxy-5-pyrazolinone; 1-ethyl-3-ethoxycarbonyl-4,4-dihydroxy-5-pyrazolinone; 1-isopropyl-4,4-dihydroxy-5-pyrazolinone; 1-isopropyl-3-methyl-4,4-dihydroxy-5-pyrazolinone; 1-isopropyl-3-phenyl-4,4-dihydroxy-5-pyrazolinone; 1-isopropyl-3-(4'-chlorophenyl)-4,4-dihydroxy-5-pyrazolinone; 1-isopropyl-3-(3'-methoxyphenyl)-4,4-dihydroxy-5-pyrazolinone; 1-isopropyl-3-(4'-methoxyphenyl)-4,4-dihydroxy-5-pyrazolinone; 1-isopropyl-3-(3'-nitrophenyl)-4,4-dihydroxy-5-pyrazolinone; 1-isopropyl-3-(4'-methylphenyl)-4,4-dihydroxy-5-pyrazolinone; 1-isopropyl-3-(2'-furyl)-4,4-dihydroxy-5-pyrazolinone; 1-isopropyl-3-(2'-thienyl)-4,4-dihydroxy-5-pyrazolinone; 1-isopropyl-3-(5'-pyrazolyl)-4,4-dihydroxy-5-pyrazolinone; 1-isopropyl-3-methoxy-4,4-dihydroxy-5-pyrazolinone; 1-isopropyl-3-ethoxy-4,4-dihydroxy-5-pyrazolinone; 1-isopropyl-3-dimethylamino-4,4-dihydroxy-5-pyrazolinone; 1-isopropyl-3-diethylamino-4,4-dihydroxy-5-pyrazolinone; 1-isopropyl-3-acetamido-4,4-dihydroxy-5-pyrazolinone; 1-isopropyl-3-carboxy-4,4-dihydroxy-5-pyrazolinone; 1-isopropyl-3-methoxycarbonyl-4,4-dihydroxy-5-pyrazolinone; 1-isopropyl-3-ethoxycarbonyl-4,4-dihydroxy-5-pyrazolinone; 1-tert-butyl-4,4-dihydroxy-5-pyrazolinone; 1-tert-butyl-3-methyl-4,4-dihydroxy-5-pyrazolinone; 1-tert-butyl-3-phenyl-4,4-dihydroxy-5-pyrazolinone; 1-tert-butyl-3-(4'-chlorophenyl)-4,4-dihydroxy-5-pyrazolinone; 1-tert-butyl-3-(3'-methoxyphenyl)-4,4-dihydroxy-5-pyrazolinone; 1-tert-butyl-3-(4'-methoxyphenyl)-4,4-dihydroxy-5-pyrazolinone; 1-tert-butyl-3-(3'-nitrophenyl)-4,4-dihydroxy-5-pyrazolinone; 1-tert-butyl-3-(4'-methylphenyl)-4,4-dihydroxy-5-pyrazolinone; 1-tert-butyl-3-(2'-furyl)-4,4-dihydroxy-5-pyrazolinone; 1-tert-butyl-3-(2'-thienyl)-4,4-dihydroxy-5-pyrazolinone; 1-tert-butyl-3-(5'-pyrazolyl)-4,4-dihydroxy-5-pyrazolinone; 1-tert-butyl-3-methoxy-4,4-dihydroxy-5-pyrazolinone; 1-tert-butyl-3-ethoxy-4,4-dihydroxy-5-pyrazolinone; 1-tert-butyl-3-dimethylamino-4,4-dihydroxy-5-pyrazolinone; 1-tert-butyl-3-diethylamino-4,4-dihydroxy-5-pyrazolinone; 1-tert-butyl-3-acetamido-4,4-dihydroxy-5-pyrazolinone; 1-tert-butyl-3-carboxy-4,4-dihydroxy-5-pyrazolinone; 1-tert-butyl-3-methoxycarbonyl-4,4-dihydroxy-5-pyrazolinone; 1-tert-butyl-3-ethoxycarbonyl-4,4-dihydroxy-5-pyrazolinone; 1-octyl-4,4-dihydroxy-5-pyrazolinone; 1-octyl-3-methyl-4,4-dihydroxy-5-pyrazolinone; 1-octyl-3-phenyl-4,4-dihydroxy-5-pyrazolinone; 1-octyl-3-(4'-chlorophenyl)-4,4-dihydroxy-5-pyrazolinone; 1-octyl-3-(3'-methoxyphenyl)-4,4-dihydroxy-5-pyrazolinone; 1-octyl-3-(4'- methoxyphenyl)-4,4-dihydroxy-5-pyrazolinone; 1-octyl-3-(3'-nitrophenyl)-4,4-dihydroxy-5-pyrazolinone; 1-(4'-methylphenyl)-4,4-dihydroxy-5-pyrazolinone; 1-(4'-methylphenyl)-3-methyl-4,4-dihydroxy-5-pyrazolinone; 1-(4'-methylphenyl)-3-phenyl-4,4-dihydroxy-5-pyrazolinone; 1-(4'-methylphenyl)-3-(4'-chlorophenyl)-4,4-dihydroxy-5-pyrazolinone; 1-(3'-methylphenyl)-3-(3'-methoxyphenyl)-4,4-dihydroxy-5-pyrazolinone; 1-(4'-methylphenyl)-3-(4'-methoxyphenyl)-4,4-dihydroxy-5-pyrazolinone; 1-(4'-methylphenyl)-3-(3'-nitrophenyl)-4,4-dihydroxy-5-pyrazolinone; 1-(4'-methylphenyl)-3-(4'-methylphenyl)-4,4-dihydroxy-5-pyrazolinone; 1-(4'-methylphenyl)-3-(2'-furyl)-4,4-dihydroxy-5-pyrazolinone; 1-(4'-methylphenyl)-3-(2'-thienyl)-4,4-dihydroxy-5-pyrazolinone; 1-(4'-methylphenyl)-3-(5'-pyrazolyl)-4,4-dihydroxy-5-pyrazolinone; 1-(4'-methylphenyl)-3-methoxy-4,4-dihydroxy-5-pyrazolinone; 1-(4'-methylphenyl)-3-ethoxy-4,4-dihydroxy-5-pyrazolinone; 1-(4'-methylphenyl)-3-dimethylamino-4,4-dihydroxy-5-pyrazolinone; 1-(4'-methylphenyl)-3-diethylamino-4,4-dihydroxy-5-pyrazolinone; 1-(4'-methylphenyl)-3-acetamido-4,4-dihydroxy-5-pyrazolinone; 1-(4'-methylphenyl)-3-carboxy-4,4-dihydroxy-5-pyrazolinone; 1-(4'-methylphenyl)-3-methoxycarbonyl-4,4-dihydroxy-5-pyrazolinone; 1-(4'-methylphenyl)-3-ethoxycarbonyl-4,4-dihydroxy-5-pyrazolinone; 1-benzyl-4,4-dihydroxy-5-pyrazolinone; 1-benzyl-3-methyl-4,4-dihydroxy-5-pyrazolinone; 1-benzyl-3-phenyl-4,4-dihydroxy-5-pyrazolinone; 1-benzyl-3-(4'-methylphenyl)-4,4-dihydroxy-5-pyrazolinone; 1-benzyl-3-(3'-methoxyphenyl)-4,4-dihydroxy-5-pyrazolinone; 1-benzyl-3-(4'-methoxyphenyl)-4,4-dihydroxy-5-pyrazolinone; 1-benzyl-3-(3'-nitrophenyl)-4,4-dihydroxy-5-pyrazolinone; 1-(4'-methoxyphenyl)-4,4-dihydroxy-5-pyrazolinone; 1-(4'-methoxyphenyl)-3-methyl-4,4-dihydroxy-5-pyrazolinone; 1-(4'-methoxyphenyl)-3-(3'-methoxyphenyl)-4,4-dihydroxy-5-pyrazolinone; 1-(4'-methoxyphenyl)-3-phenyl-4,4-dihydroxy-5-pyrazolinone; 1-(4'-methoxyphenyl)-3-(4'-chlorophenyl)-4,4-dihydroxy-5-pyrazolinone; 1-(4'-methoxyphenyl)-3-(4'-methoxyphenyl)-4,4-dihydroxy-5-pyrazolinone; 1-(4'-methoxyphenyl)-3-(3'-nitrophenyl)-4,4-dihydroxy-5-pyrazolinone; 1-(4'-methoxyphenyl)-3-methoxy-4,4-dihydroxy-5-pyrazolinone; 1-(4'-methoxyphenyl)-3-ethoxy-4,4-dihydroxy-5-pyrazolinone; 1-(4'-methoxyphenyl)-3-dimethylamino-4,4-dihydroxy-5-pyrazolinone; 1-(4'-methoxyphenyl)-3-diethylamino-4,4-dihydroxy-5-pyrazolinone; 1-(4'-methoxyphenyl)-3-acetamido-4,4-dihydroxy-5-pyrazolinone; 1-(4'-methoxyphenyl)-3-carboxy-4,4,-dihydroxy-5-pyrazolinone; 1-(4'-methoxyphenyl)-3-methoxycarbonyl-4,4 dihydroxy-5-pyrazolinone; 1-(4'-methoxyphenyl)-3-ethoxycarbonyl-4,4-dihydroxy-5-pyrazolinone; 1-(4'-chlorophenyl)-4,4-dihydroxy-5-pyrazolinone; 1-(4'-chlorophenyl)-3-methyl-4,4-dihydroxy-5-pyrazolinone; 1-(4'-chlorophenyl)-3-phenyl-3-4,'4-dihydroxy-5-pyrazolinone; 1-(4'-chlorophenyl)-3-(4'-methylphenyl)-4,4dihydroxy-5-pyrazolinone; 1-(4'-chlorophenyl)-3-(3'-methoxyphenyl-4,4-dihydroxy-5-pyrazolinone; 1-(4'-chlorophenyl)-3-(4'-methoxyphenyl)-4,4-dihydroxy-5-pyrazolinone; 1-(4'-chlorophenyl)-3-(3'-nitrophenyl)-4,4-dihydroxy-5-pyrazolinone; (1-(4'-chlorophenyl)-3-methoxy-4,4-dihydroxy-5-pyrazolinone; 1-(4'-chlorophenyl)-3-ethoxy-4,4-dihydroxy-5-pyrazolinone; 1-(4'-chlorophenyl)-3-dimethylamino-4,4-dihydroxy-5-pyrazolinone; 1-(4'-chlorophenyl)-3-diethylamino-4,4-dihydroxy-5-pyrazolinone; 1-(4'-chlorophenyl)-3-acetamido-4,4-dihydroxy-5-pyrazolinone; 1-(4'-chlorophenyl)-3-carboxy-4,4-dihydroxy-5-pyrazolinone; 1-(4'-chlorophenyl)-3-methoxycarbonyl-4,4-dihydroxy-5-pyrazolinone; 1-(4'-chlorophenyl)-3-ethoxycarbonyl-4,4-dihydroxy-5-pyrazolinone; 1-(4'-nitrophenyl)-4,4-dihydroxy-5-pyrazolinone; 1-(4'-nitrophenyl) -3-methyl-4,4-dihydroxy-5-pyrazolinone; 1-(4'-nitrophenyl)-3-phenyl-4,4-dihydroxy-5-pyrazolinone; 1-(4'-nitrophenyl)-3-(4'-methylphenyl)-4,4-dihydroxy-5-pyrazolinone; 1-(4'-nitrophenyl)-3-(3'-methoxyphenyl) -4,4-dihydroxy-5-pyrazolinone; 1-(4'-nitrophenyl)-3-(4'-methoxyphenyl)-4,4-dihydroxy-5-pyrazolinone; 1-(4'-nitrophenyl)-3-(3'-nitrophenyl)-4,4-dihydroxy-5-pyrazolinone; 1-phenyl-3-trifluoromethyl-4,4-dihydroxy-5-pyrazolinone; 1-methyl-3-trifluoromethyl-4,4-dihydroxy-5-pyrazolinone; 1-isopropyl-3-trifluoromethyl-4,4-dihydroxy-5-pyrazolinone; 1-ethyl-3-trifluoromethyl-4,4-dihydroxy-5-pyrazolinone; and 3-trifluoromethyl-4,4-dihydroxy-5-pyrazolinone.

4. The 4,4-dihydroxy-5-pyrazolinone compound as defined by claim 1, wherein formula (I), $R_1$ is hydrogen or a methyl, ethyl, isopropyl, tert-butyl or substituted or unsubstituted phenyl radical; and $R_2$ is a hydrogen or a methyl, phenyl, methoxyphenyl, methoxy, etehoxy, carboxyl, methoxycarbonyl, ethoxycarbonyl, acetamido, dimethylamino, diethylamino, trifluoromethyl, furyl or pyridyl radical.

5. The 4,4-dihydroxy-5-pyrazolinone compound as defined by claim 1, selected from among 3-methyl-4,4-dihydroxy-5-pyrazolinone; 1,3-dimethyl-4,4-dihydroxy-5-pyrazolinone; 1-ethyl-3-methyl-4,4-dihydroxy-5-pyrazolinone; 1-isopropyl-3-methyl-4,4-dihydroxy-5-pyrazolinone; 1-tert-butyl-3-methyl-4,4-dihydroxy-5-pyrazolinone; 1-methyl-3-phenyl-4,4-dihydroxy-5-pyrazolinone; 1-methyl-3-(3'-methoxyphenyl)-4,4-dihydroxy-5-pyrazolinone; 3-(2'-furyl)-1-methyl-4,4-dihydroxy-5-pyrazolinone; 1-methyl-3-(4'-pyridyl)-4,4-dihydroxy-5-pyrazolinone; 1-methyl-3-methoxy-4,4-dihydroxy-5-pyrazolinone; 3-ethoxy-1-methyl-4,4-dihydroxy-5-pyrazolinone; 3-dimethylamino-1-methyl-4,4-dihydroxy-5-pyrazolinone; 3-diethylamino-1-methyl-4,4-dihydroxy-5-pyrazolinone; 3-acetamido-1-methyl-4,4-dihydroxy-5-pyrazolinone; 1-phenyl-4,4-dihydroxy-5-pyrazolinone; 1-methyl-4,4-dihydroxy-5-pyrazolinone; 1-ethyl-4,4-dihydroxy-5-pyrazolinone; 1-isopropyl-4,4-dihydroxy-5-pyrazolinone; 1-tert-butyl-4,4-dihydroxy-5-pyrazolinone; 3-methoxy-1-phenyl-4,4-dihydroxy-5-pyrazolinone; 3-ethoxy-1-phenyl-4,4-dihydroxy-5-pyrazolinone; 3-acetamido-1-phenyl-4,4-dihydroxy-5-pyrazolinone; 3-dimethylamino-1-phenyl-4,4-dihydroxy-5-pyrazolinone; 3-diethylamino-1-phenyl-4,4-dihydroxy-5-pyrazolinone; 1-phenyl-3-trifluoromethyl-4,4-dihydroxy-5-pyrazolinone; 1-methyl-3-trifluoromethyl -4,4-dihydroxy-5-pyrazolinone; 1-isopropyl-3-trifluoromethyl-4,4-dihydroxy-5-pyrazolinone; 1-ethyl-3-trifluoromethyl-4,4-dihydroxy-5-pyrazolinone; 3-trifluoromethyl-4,4-dihydroxy-5-pyrazolinone; 3-carboxy-1-phenyl-4,4-dihydroxy-5-pyrazolinone; 3-methoxycarbonyl-1-phenyl-4,4- dihydroxy-5-pyrazolinone; 3-ethoxycarbonyl-1-phenyl -4,4-dihydroxy-5-pyrazolinone; 3-methoxy-4,4-dihydroxy-5-pyrazolinone; 3-ethoxy-4,4-dihydroxy-5-pyrazolinone; 3-carboxy-1-methyl-4,4-dihydroxy-5-pyrazolinone; 3-methoxycarbonyl-1-methyl-4,4-dihydroxy -5-pyrazolinone; and 3-ethoxycarbonyl -1-methyl-4,4-dihydroxy-5-pyrazolinone.

6. A topically applicable cosmetic/dermatological composition adopted for the artificial tanning and/or coloring of human skin and/or hair, comprising an effective artificial tanning/coloring amount of at least one 4,4-dihydroxy-5- pyrazolinone as defined by claim 1, formulated into a topically applicable, cosmetically/dermatologically acceptable vehicle, diluent or carrier therefor.

7. The cosmetic/dermatological composition as defined by claim 6, comprising from 0.05% to 10% by weight of said at least one 4,4-dihydroxy-5-pyrazolinone.

8. The cosmetic/dermatological composition as defined by claim 6, formulated as an emulsion, cream, lotion, gel, cream-gel, mousse, powder, solid, or spray.

9. The cosmetic/dermatological composition as defined by claim 6, formulated as a makeup.

10. The cosmetic/dermatological composition as defined by claim 6, formulated as a hair dye.

11. A regime or regimen for artificially tanning and/or coloring human skin and/or hair, comprising topically applying thereto an effective amount of the cosmetic/dermatological composition as defined by claim 6.

12. A regime or regimen for imparting a healthy appearance to human facial skin by enhancing the radiance of the complexion thereof, while at the same time retaining transparency, comprising topically applying thereto an effective amount of the cosmetic/dermatological composition as defined by claim 6.

13. A process for the preparation of the 4,4-dihydroxy-5-pyrazolinone as defined by claim 1, comprising:

(i) reacting a monosubstituted hydrazine $R_1NH-NH_2$ with a β-keto ester of the structure:

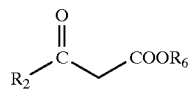

in which $R_6$ is a linear or branched $C_1-C_4$ alkyl radical, optionally in alcoholic medium, at a temperature ranging from 65° to 85° C., to obtain a 5-pyrazolinone (1), which is then reacted with an aromatic nitroso compound (2) to obtain the corresponding 4-arylimino-5-pyrazolinone (3):

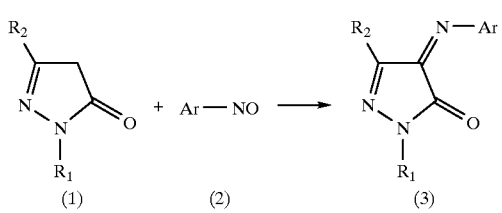

this reaction being carried out in a lower alcohol, at a temperature ranging from 65° C. to 85° C., at the reflux point of the solvent used, and optionally in the presence of a catalytic amount of a weak base, and (ii) then hydrolyzing the 4-arylimino-5-pyrazolinone (3), optionally in dilute strong acid medium, to obtain the corresponding 4,4-dihydroxy-5-pyrazolinone derivative of formula (I):

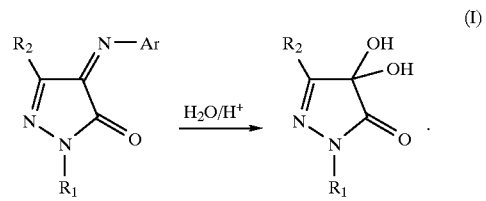

14. The process as defined by claim 13, said step (i) aromatic nitroso compound (2) having the formula:

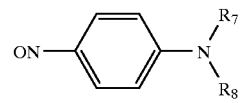

in which $R_7$ and $R_8$ are each a linear or branched $C_1-C_4$ alkyl radical.

15. The process as defined by claim 13, comprising conducting said acid hydrolysis step (ii) with dilute sulfuric acid or aqueous hydrochloric acid in the presence of a co-solvent for the 4,4-dihydroxy-5-pyrazolinone which is immiscible with water.

16. The process as defined by claim 15, said co-solvent comprising diethyl ether or diisopropyl ether.

* * * * *